United States Patent
Vehkamäki et al.

(10) Patent No.: US 7,618,681 B2
(45) Date of Patent: Nov. 17, 2009

(54) PROCESS FOR PRODUCING BISMUTH-CONTAINING OXIDE FILMS

(75) Inventors: Marko Vehkamäki, Helsinki (FI); Timo Hatanpää, Helsinki (FI); Mikko Ritala, Espoo (FI); Markku Leskelä, Espoo (FI)

(73) Assignee: ASM International N.V. (NL)

( * ) Notice: Subject to any disclaimer, the term of this patent is extended or adjusted under 35 U.S.C. 154(b) by 282 days.

(21) Appl. No.: 10/696,591

(22) Filed: Oct. 28, 2003

(65) Prior Publication Data
US 2005/0089632 A1    Apr. 28, 2005

(51) Int. Cl.
C23C 16/00    (2006.01)
C23C 16/40    (2006.01)
C23C 16/06    (2006.01)

(52) U.S. Cl. .............. 427/248.8; 427/255.32; 427/255.31; 427/255.395; 427/255.28; 427/249.15; 427/255.18; 427/255.19

(58) Field of Classification Search .............. 427/248.1, 427/249.15, 255.18, 255.19, 255.28, 255.395, 427/255.31, 255.32
See application file for complete search history.

(56) References Cited

U.S. PATENT DOCUMENTS

| | | | | |
|---|---|---|---|---|
| 5,276,010 | A | * | 1/1994 | Sasaki .................. 505/476 |
| 5,496,582 | A | | 3/1996 | Mizutani et al. |
| 5,902,639 | A | * | 5/1999 | Glassman et al. ........ 427/248.1 |
| 5,972,430 | A | | 10/1999 | DiMeo, Jr. et al. |
| 6,177,135 | B1 | * | 1/2001 | Hintermaier et al. ... 427/255.31 |
| 6,537,613 | B1 | | 3/2003 | Senzaki et al. |
| 6,849,305 | B2 | | 2/2005 | Bravo-Vasquez et al. |
| 7,045,430 | B2 | | 5/2006 | Ahn et al. |
| 2003/0124875 | A1 | * | 7/2003 | Kil .............................. 438/785 |
| 2004/0028811 | A1 | * | 2/2004 | Cho et al. ................ 427/248.1 |
| 2006/0228888 | A1 | | 10/2006 | Lee et al. |

FOREIGN PATENT DOCUMENTS

| | | | | |
|---|---|---|---|---|
| WO | WO 02/27063 | * | 4/2002 | ............ 427/255.29 |
| WO | WO 02/27063 A2 | | 4/2002 | |

OTHER PUBLICATIONS

Shin et al., "Plasma-Enhanced Atomic Layer Deposition of $SrTa_2O_6$ and $SrBi_2Ta_2O_9$ Thin Films"; Atomic Layer Deposition (ALD 2002) Conference, Hanyang University, Seoul Korea, Aug. 19-21, pp. 1-18 (2002).

(Continued)

*Primary Examiner*—Timothy Meeks
*Assistant Examiner*—Kelly M Gambetta
(74) *Attorney, Agent, or Firm*—Knobbe, Martens, Olson & Bear LLP

(57) ABSTRACT

A process for producing bismuth-containing oxide thin films by Atomic Layer Deposition, including using an organic bismuth compound having at least one silylamido ligand as a source material for the bismuth oxide. Bismuth-containing oxide thin films produced by the preferred embodiments can be used, for example, as ferroelectric or dielectric material in integrated circuits and/or as superconductor materials.

32 Claims, 2 Drawing Sheets

OTHER PUBLICATIONS

Williams et al. "Crystal Structure of $Bi(OCMe_2CH_2Ome)_3$ and Its Use in the MOCVD of $Bi_2O_3$**"; Chemical Vapor Deposition; pp. 205-206 (2001).

Gordon et al. "Vapor Deposition of Metal Oxides and Silicates: Possible Gate Insulators for Future Microelectronics"; Chem. Mater.; vol. 13; pp. 2463-2464 (2001).

Ritala et al. Chapter 2, "Atoic Layer Disposition"; Handbook of Thin Film Materials; vol. 1: Deposition and Processing of Thin Films; pp. 103-159 (2002).

Leskela et al., "ALD precursor chemistry: Evolution and future challenges," *J. Phys. IV France* 9: 837-847 (1999).

Office Action for U.S. Appl. No. 11/221,574 dated Oct. 16, 2008.

* cited by examiner

PROCESS FOR PRODUCING BISMUTH-CONTAINING OXIDE FILMS

BACKGROUND OF THE INVENTION

1. Field of the Invention

The invention generally relates to bismuth-containing oxide films. In particular, the present invention relates to a process for manufacturing bismuth-containing oxide thin films by Atomic Layer Deposition (ALD).

2. Description of the Related Art

Bismuth is a component of several technologically important binary and multicomponent oxide thin film materials, particularly the ferroelectric oxides $Bi_4Ti_3O_{12}$, $(Bi,La)_4Ti_3O_{12}$, and $SrBi_2Ta_2O_9$ and, also, the superconducting oxide $Bi_2Sr_2CaCu_2O_{8+x}$. Ferroelectric bismuth oxide films have great potential use in ferroelectric memory cells. In such uses, the films are likely to be formed with capacitors in the form of 3-D structures, which means that good conformality of the ferroelectric film is desired to ensure proper function of the memory cell.

Atomic Layer Deposition, in the following also abbreviated "ALD", is a deposition method in which a product, such as a thin film, is deposited on a substrate from precursors in the vapor phase. ALD is based on sequential self-saturated surface reactions. The characteristics of an ALD process are described in detail in U.S. Pat. Nos. 4,058,430 and 5,711,811 which are incorporated herein. The reactors designed for ALD benefit from the usage of inert carrier and purging gases, which makes the system faster.

According to the principles of the ALD, the source chemicals (or "precursors") are separated from each other by inert gases (i.e., by purging) which substantially prevents gas-phase reactions between gaseous reactants, thereby facilitating the film growth by the above-mentioned self-saturated surface reactions. Advantageously, ALD requires neither strict temperature control of the substrates nor precise dosage control of source chemicals. Surplus chemicals and reaction by-products are removed from the reaction chamber before the next reactive chemical pulse is introduced into the chamber. Undesired gaseous molecules are effectively expelled from the reaction chamber by keeping the gas flow speeds high with the help of an inert purging gas. The purging gas pushes the extra molecules towards the vacuum pump used for maintaining a suitable pressure in the reaction chamber. Advantageously, ALD provides an excellent and automatic self-control for the film growth as well as outstanding conformality.

Based on its general properties, ALD is a potentially attractive alternative for deposition of bismuth-containing oxide thin films. However, prior art attempts at the deposition of bismuth containing oxides by ALD had a number of shortcomings. The main problem has been finding appropriate bismuth-oxygen source combinations for depositing bismuth oxide. In an earlier article[M. Schuisky et al., Chem. Vap. Deposition 6 (2000) 139], triphenyl bismuth, a commonly used CVD precursor, was examined for depositing $Bi_4Ti_3O_{12}$. No binary $Bi_2O_3$ could be deposited, but bismuth could be incorporated into Bi—Ti—O mixture films. However, the levels were too low for forming the desired $Bi_4Ti_3O_{12}$ phase. Application of $BiCl_3$ and water, in turn, has resulted in a BiOCl phase (M. Schuisky et al.). Trimethyl bismuth is another common bismuth (Bi) CVD precursor, but it is reported to be explosive. Quite recently, $Bi(OCMe_2CH_2OMe)_3$ was introduced as a new Bi CVD precursor [P. A. Williams, Chem. Vap. Deposition 7 (2001) 205]. The present inventors tested this compound in ALD and found that it decomposes too easily when heated inside the reactor. Other tested compounds include $Bi(CH_2SiMe_3)_3$, for which no film growth has been observed with water as an oxygen source, and $Bi(thd)_3$, which appears to be quite unstable based on TG measurements.

In their paper, Roy Gordon et al. (Chem. Mater. 13 (2001) 2463) reported the use of La silylamide for deposition of the corresponding oxide and a mixture of said compound with silicon oxide. The article further contains—it would appear—an exhaustive list of elements forming volatile silylamides. The article is, however, silent about the use of bismuth-containing silylamides.

As the above surveys show, there are no satisfactory processes known for producing bismuth-containing ferroelectric films by the Atomic Layer Deposition technique.

SUMMARY OF THE INVENTION

It is an object of preferred embodiments of the invention to reduce the problems of the prior art and to provide a novel ALD process for producing bismuth-containing oxide thin films.

It is another object of preferred embodiments of the invention to provide binary and multicomponent oxide thin films containing bismuth and other metals for use as ferroelectric and dielectric materials and/or in superconductor applications.

These and other objects, together with the advantages thereof over known processes and products, are achieved by preferred embodiments of the present invention as hereinafter described and claimed.

According to a preferred embodiment of the present invention, it has been found that a specific group of organic bismuth compounds can be used as precursors for producing bismuth-containing oxide thin films (binary as well as multicomponent oxides of bismuth). The organic bismuth compounds of the preferred embodiments have in common that they all contain substituted silylamide ligands. The finding was surprising because silylamides are not known for being particularly stable compounds, and —as mentioned above in connection with the article by Roy Gordon et al.—there are no indications in the art of their applicability in ALD.

A preferred embodiment of the invention comprises a novel process for producing bismuth-containing oxide thin films, in which organic bismuth compounds having at least one bis(trialkylsilyl)amido ligand are used as precursors for depositing films by Atomic Layer Deposition. In such a preferred process, vapor phase pulses of an organic bismuth compound having at least one bis(trialkylsilyl)amido ligand as a source material of bismuth oxide and at least one oxygen source material capable of forming an oxide with the source material, are alternately fed into a reaction space containing a suitable substrate in order to deposit bismuth-containing oxide thin films.

By introducing into the reaction space vapor phase pulses of a second source material, containing at least one transition metal or main group metal, followed by suitable pulses of an oxygen source material, it is possible to produce ternary and other multicomponent bismuth oxide films.

According to one aspect of the invention, a process for producing a bismuth-containing oxide thin film by Atomic Layer Deposition (ALD) is provided. In this ALD process an organic bismuth compound having at least one silylamido ligand is used as a source material for the bismuth-containing oxide thin film.

According to another aspect of the invention, a process for depositing a bismuth oxide layer on a substrate by Atomic Layer Deposition (ALD) is provided. A vapor phase pulse of an organic bismuth compound source material having at least one bis(trialkylsilyl)amido ligand is fed into a reaction space. A pulse of an oxygen source material capable of forming an oxide with the organic bismuth compound source material is then pulsing into the reaction space. In certain embodiments, this process includes pulsing a second metal source into the reaction space to form a multi-component film, such as a ternary film.

Considerable advantages are obtained by the preferred embodiments. Thus, the novel ALD source materials, exemplified by tris(bis(trialkylsilyl)amido) bismuth(III), have been tested and found to work well as precursors for both binary and multicomponent oxides of bismuth. The properties of this novel precursor group are illustrated below by tris(bis(trimethylsilyl)-amido)bismuth(III) [in the following abbreviated Bi(btsa)$_3$]. Bi(btsa)$_3$ is a volatile compound, which is stable at a temperature range compatible with ranges used for the ALD deposition using precursors of many other metal components in bismuth-containing multi-component oxide materials. Therefore, the preferred embodiments make it possible to deposit thin films by ALD, while operating the process at conditions under which Bi(btsa)$_3$ is stable.

Films deposited by a preferred embodiment exhibit good thin films properties, e.g., they have excellent conformality even on uneven surfaces. As a result, the novel films can be used in 3-D folding and/or roughened capacitors. The invention also provides for excellent and automatic self-control of film growth.

Bismuth-containing oxide thin films produced by the preferred embodiments can be used, for example, as ferroelectric or dielectric material in integrated circuits and/or superconductor materials.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

Next, the preferred embodiments are described in detail with the aid of the following detailed description and by reference to the attached drawings.

DETAILED DESCRIPTION OF THE PREFERRED EMBODIMENT

Figure 1:
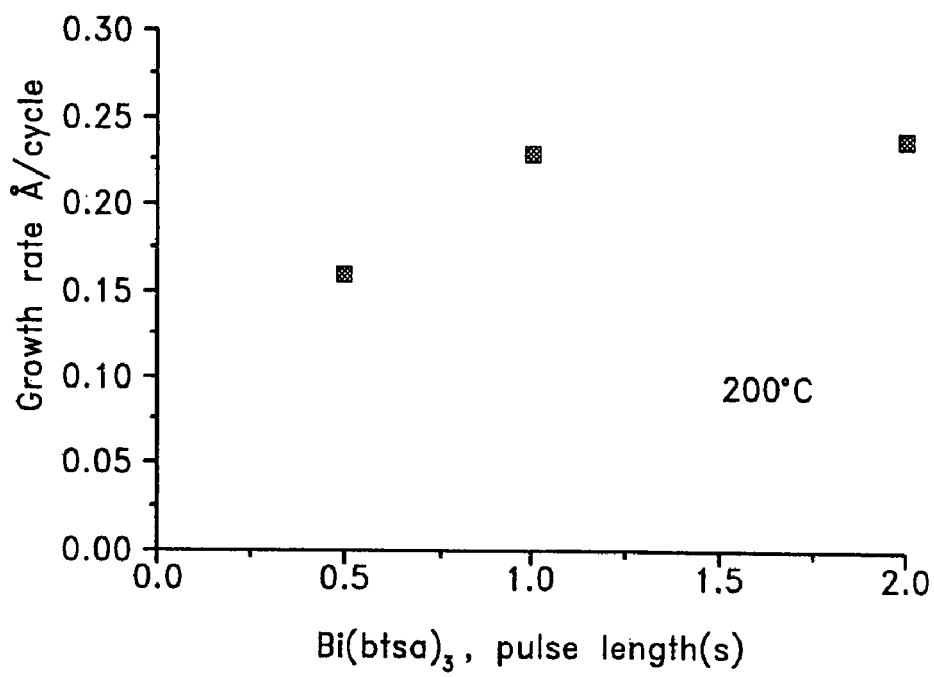
FIG. 1 shows graphically the experimental results obtained in the working example below of the saturation of the Bi—O growth rate from Bi(btsa)$_3$ and water at 200° C.

In context of the preferred embodiments, "an ALD type process" generally refers to a process for producing thin films over a substrate in which a solid thin film is formed molecular layer by molecular layer due to self-saturating chemical reactions on heated surfaces. In the ALD process, gaseous vapor phase reactants, are conducted into a reaction chamber of an ALD reactor and contacted with a substrate located in the chamber to provide a surface reaction. The pressure and the temperature of the reaction chamber are adjusted to a range where physisorption (i.e., condensation) and thermal decomposition of the reactants are avoided. Consequently, only up to one monolayer (i.e., an atomic layer or a molecular layer) of material is deposited at a time during each pulsing cycle. The actual growth rate of the thin film, which is typically presented as Å/pulsing cycle, depends, for example, on the number of available reactive surface sites on the surface and bulkiness of the chemisorbing molecules. Gas phase reactions between precursors and any undesired reactions of by-products are inhibited because material pulses are separated from each other by time and the reaction chamber is purged with an inactive gas (e.g., nitrogen or argon) between material pulses to remove surplus gaseous vapor phase reactants and reaction by-products from the chamber. The principles of ALD type processes have been presented by Dr T. Suntola, e.g., in the Handbook of Crystal Growth 3, Thin Films and Epitaxy, Part B: Growth Mechanisms and Dynamics, Chapter 14, Atomic Layer Epitaxy, pp. 601-663, Elsevier Science B.V. 1994, the disclosure of which is incorporated herein by reference.

Extensive selection of ALD precursors and ALD-grown materials have been presented by Prof. M. Ritala and Prof. M. Leskelä in a recent review article, Handbook of Thin Film Materials, Vol. 1: Deposition and Processing of Thin Films, Chapter 2 "Atomic Layer Deposition", pp. 103-159, Academic Press 2002.

In context of the present application "a reaction space" generally designates a reactor or a reaction chamber in which the conditions can be adjusted so that deposition of a thin film is possible.

In context of the present application, "an ALD type reactor" means a reactor where the reaction space is in fluid communication with an inactive gas source and at least one, preferably at least two precursor sources that can be pulsed, the reaction space is in fluid communication with a vacuum generator (e.g., a vacuum pump), and the temperature and pressure of the reaction space and the flow rates of gases can be adjusted to a range that makes it possible to grow thin films by ALD type processes.

As known in the art, there are various variations of the basic ALD method, including PEALD (plasma enhanced ALD) in which plasma is used for activating reactants. Conventional ALD or thermal ALD refers to an ALD method where plasma is not used but where the substrate temperature is high enough for overcoming the energy barrier (activation energy) during collisions between the chemisorbed species on the surface and reactant molecules in the gas phase so that up to a molecular layer of thin film grows on the substrate surface during each ALD pulsing sequence. For the purpose of the preferred embodiments, ALD covers both PEALD and thermal ALD.

"Source material" and "precursor" are used interchangeably to designate a volatile or gaseous metal compound, which can be used as a starting compound for the corresponding metal oxide of the thin film. Reactants can include "precursors" (which leave a component on the film), but can also include, e.g., reducing agents.

The term "multicomponent oxide" covers oxide materials formed by at least two different metal cations.

According to certain preferred embodiments, bismuth precursors containing at least one, preferably 1 to 3, silylamido ligand(s) is/are used as source materials in production of thin films in ALD reactors. The precursors preferably contain three silylamido ligands. Such compounds are exemplified by tris(bis(trialkylsilyl)amido) bismuth(III), wherein the "alkyl" stands for a lower alkyl group, selected from methyl, ethyl, n- and i-propyl, and n-, sec- and t-butyl. In each ligand, and in different ligands, the alkyl groups may be same or different.

A specific example of the present novel precursors is tris (bis(trimethylsilyl)amido)bismuth(III) (Bi(btsa)$_3$) having the below formula:

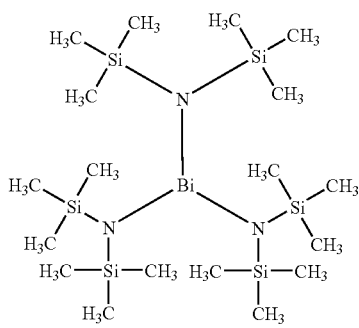

Other suitable compounds are, for example, tris(bis(ethyldimethylsilyl)amido)bismuth(III), tris(bis(n-butyldimethylsilyl)amido)bismuth(III), tris(bis(triethylsilyl)amido)bismuth(III) and tris(bis(tri-n-propylsilyl)amido)bismuth(III). Although trialkylsilylamido compounds of bismuth are preferred as ALD reactants, versatile chemistry related to silylamido molecule makes it possible to replace one or more alkyl groups in the trialkylsilylamido molecule with other substitutions. Thus, in general, the ligand has a formula according to Equation 1:

  (Equation 1)

in which each $R^1$, $R^2$, $R^3$ is independently selected from
linear or branched $C_1$-$C_{20}$ alkyl or alkenyl groups, preferably methyl, ethyl, n- and i-propyl, n-, sec- and t-butyl,
halogenated alkyl or alkenyl groups, wherein at least one hydrogen atom is replaced with a fluorine, chlorine, bromine or iodine atom,
carbocyclic groups such as aryl, preferably phenyl, alkylaryl, halogenated carbocyclic groups, and
heterocyclic groups.

In addition to alkyl, ligands contain carbocyclic structures, such as aryls, ligands, e.g., phenyl groups ($C_6H_5$—), are preferred for use as silylamido compounds in ALD. Also, halogenated silylamido compounds, including fluorinated trialkylsilylamido compounds, are considered advantageous ALD reactants. In such fluorinated compounds at least one hydrogen atom has been replaced with a fluorine atom.

Of the above mentioned precursors, the particularly preferred ones, namely the tris(bis(trialkylsilyl)amido)bismuth (III) compounds, are stable at least up to about 220° C. and can generally be used in ALD processing at temperatures below about 250° C., typically below about 225° C., suitably at about 100° C. to about 220° C., and preferably at about 150° C. to about 200° C. According to the invention, gas phase pulses of the evaporated silylamido bismuth compound are introduced into an ALD reactor, in which they are contacted with a suitable substrate. The deposition can be carried out at normal pressure, but it is preferred to operate the method at reduced pressure. The pressure in the reactor is typically 0.01-20 mbar, preferably 0.1-5 mbar. The substrate temperature is preferably low enough to keep the bonds between thin film atoms intact and to prevent thermal decomposition of the gaseous reactants. On the other hand, the substrate temperature is preferably high enough to keep the source materials in gaseous phase, i.e., condensation of the gaseous reactants should be avoided. Further, the temperature (or the energy source) must be sufficiently high to provide the activation energy for the surface reaction. Optionally, an inactive gas is used as a carrier gas during deposition.

At these conditions, the amount of reactants bound to the surface will be determined by the reactive sites available at the surface. This phenomenon is called "self-saturation".

For further details on the operation of a typical ALD process, reference is made to the documents cited above.

The substrate can be of various types. Examples include silicon, silica, coated silicon, germanium, silicon-germanium alloys, copper metal, noble and platinum metals group including silver, gold, platinum, palladium, rhodium, iridium and ruthenium, various nitrides, such as transition metal nitrides (e.g., tantalum nitride TaN), various carbides, such as transition metal carbides (e.g., tungsten carbide WC), and nitride carbides (e.g., tungsten nitride carbide $WN_xC_y$). Conventionally, the preceding thin film layer deposited will form the substrate surface for the next thin film. For both ferroelectric capacitor structures and superconductor applications, bismuth-containing films are generally deposited on appropriately patterned metal surfaces (electrodes).

In order to convert the adsorbed bismuth precursor into bismuth oxide, the reactor is purged with a purge gas such as an inactive gas, and then a next vapor phase pulse of an oxygen source material is introduced into the reactor. The oxygen source material is preferably selected from the group of water, oxygen, hydrogen peroxide, aqueous solution of hydrogen peroxide, ozone, oxides of nitrogen, halide-oxygen compounds, peracids (—O—O—H), alcohols, alkoxides, oxygen-containing radicals and mixtures thereof.

By alternating the reactions of the bismuth precursor and the oxygen source material, a bismuth-containing oxide thin film can be deposited. Typically, a growth rate of about 0.20 to 0.30 Å/cycle is achieved.

In order to produce multicomponent oxide films, a second metal source material can be introduced under ALD conditions. Such a precursor can be metal compound or a complex metal compound comprising two or several metals. The metals are typically selected from the group of volatile or gaseous compounds of transition metals and main group metals, i.e., elements of groups 1, 2, 3, 4, 5, 6, 7, 8, 9, 10, 11, 12, 13 and/or 14 (according to the system recommended by IUPAC) in the periodic table of elements.

Since the properties of each metal compound vary, the suitability of each metal compound for the use in the process of the preferred embodiments should be considered. The properties of the compounds are found, e.g., in N. N. Greenwood and A. Eamshaw, *Chemistry of the Elements*, 1$^{st}$ edition, Pergamon Press, 1986.

Typically, suitable metal source materials can be found among halides, preferably fluorides, chlorides, bromides or iodides, or metal organic compounds, preferably alkoxy (See the titanium alkoxide of Example 4), alkylamino, cyclopentadienyl, dithiocarbamate or betadiketonate compounds of the desired metal(s). Also double metal precursors, i.e., molecules containing two metals in a discrete ratio, may be used (See Example 2 below).

In a preferred embodiment of the present invention, a multicomponent oxide film consists essentially of Bi, Ca, Sr, Cu, Ti, Ta, Zr, Hf, V, Nb, Cr, W, Mo, Al, Si and/or Pb oxide(s) and, thus, the corresponding gaseous or volatile compounds are preferably used. The second metal source material can be oxidized using the same or another oxygen source material as for the bismuth precursor. For example, the multicomponent oxide film can be $Bi_4Ti_3O_{12}$, $(Bi,La)_4Ti_3O_{12}$, $SrBi_2Ta_2O_9$ or $Bi_2Sr_2CaCu_2O_{8+x}$.

In certain preferred embodiments, aluminium and silicon are particularly interesting as sources of a second and/or third metal in ternary and other multicomponent bismuth-containing oxides. Multicomponent Bi/Al and/or Si oxides are potentially valuable, as high-k dielectric material. In other preferred embodiments, the ternary oxide thin film consists of a second metal such as copper, titanium, tantalum, calcium, strontium, silicon, or aluminum.

According to one preferred embodiment, multicomponent films are produced by feeding alternating pulses of the various metal precursors (followed by the above mentioned oxygen source pulses) into an ALD reactor. This embodiment based on "mixing cycles" will give rise to a ferroelectric phase after deposition. Typically, the ratio of first cycles (consisting of bismuth-containing precursor followed by oxygen source pulses) to second cycles (consisting of a second metal source followed by the corresponding oxygen source pulses) is about 20:1 to about 1:20, preferably about 10:1 to 1:10, more preferably about 6:1 to about 1:3. A stoichiometric surplus of about 1 to 20 atomic percentage of bismuth in the films is advantageous for some applications, particularly including $SrBi_2Ta_2O_9$. An example of this embodiment is given in Example 2 below.

Another preferred embodiment comprises preparing multicomponent films by depositing laminar layers of each metal oxide and annealing the laminar layers together at increased temperatures to provide a ferroelectric phase. In this way, an amorphous structure is first provided and the ferroelectric phase can be obtained by annealing in the presence of oxygen (such as in the presence of air) at temperatures in excess of 500° C., in particular in excess of 700° C. The advantage of this embodiment is that the composition of the films can be controlled by adjusting the thickness of the laminar layers. This embodiment is illustrated in Example 3 below.

A third preferred embodiment for preparing binary films comprises a combination of the above described embodiments. Thus, the cycle mixing approach can be used for producing a mixed bismuth-titanium, bismuth-tantalum or bismuth-hafnium oxide film. If the film is amorphous, it can be annealed at the temperatures mentioned above, in the presence of air or another oxygen-containing gas.

In the above embodiments, where a second and possibly further metal precursors are fed into an ALD reactor, a vapor phase pulse of an oxygen source material is preferably, but not necessarily, fed into the ALD reactor after each metal precursor pulse and optionally after the purge gas pulse following the metal precursor pulse.

The present novel thin film oxide materials will find extensive application in the semiconductor industry as ferroelectric materials for nonvolatile memories. The production of Bi-containing superconductor films is also of interest in the superconductor device industry.

The following non-limiting examples illustrate certain preferred embodiments of the invention. They were carried out in an F-120™ ALD reactor supplied by ASM Microchemistry Oy, Espoo.

Tris(bis(trimethylsilyl)amido)bismuth(III) was basically synthesized as described by Carmalt et al. [C. J. Carmalt, N. A. Compton, R. J. Errington, G. A. Fisher, I. Moenandar, N. C. Norman, *Inorganic Synthesis*, 1997, 31, 98-101]. Thus, $BiCl_3$ was reacted with $Li(N(SiMe_3)_2)$ to yield the desired compound. However, the method of Carmalt et al. was modified by using pure THF as a solvent in the synthesis step instead of the solvents, $Et_2O$ and mixture of $Et_2O$ and THF, proposed in the article. Further, the reaction was also carried out at lower temperature (−12° C. vs. 0° C.) and, instead of pentane, hexane was used to dissolve the crude product before filtration. The final product was as described in the article and the yield was somewhat better.

The other reagents are commercially available.

EXAMPLE 1

ALD Growth of $Bi_2O_3$ from $Bi(btsa)_3$ and $H_2O$ was carried out at temperatures in the range of from 150 to 200° C. At deposition temperatures of 225° C. and above, no significant growth was observed, probably due to precursor decomposition. At 200° C. the Bi—O growth rate saturates at 0.23 Å/cycle (FIG. 1).

EXAMPLE 2

Figure 2:
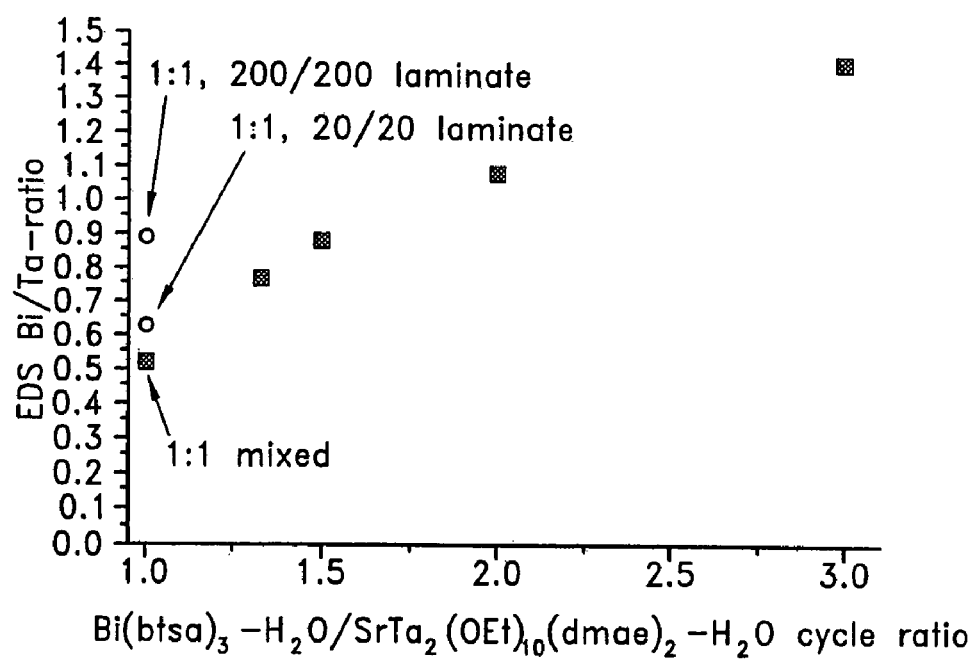
FIG. 2 shows graphically the effect on the Bi/Ta ratio of a SrBi$_2$Ta$_2$O$_9$ film obtained by changing the cycle ratio and effect of layer thicknesses at a 1:1 cycle ratio.

$SrBi_2Ta_2O_9$ films were deposited at 200° C. by mixing $[Bi(btsa)_3\text{-}H_2O]$ and $[SrTa_2(OEt)_{10}(dmae)_2\text{-}H_2O]$ cycles (FIG. 2). Average growth rates were roughly 0.2 Å/cycle. At a 2:1 cycle mixing ratio, films were obtained having 8 atomic percentage Bi in excess of stoichiometric. This composition is suitable for ferroelectric applications.

EXAMPLE 3

Figure 3:
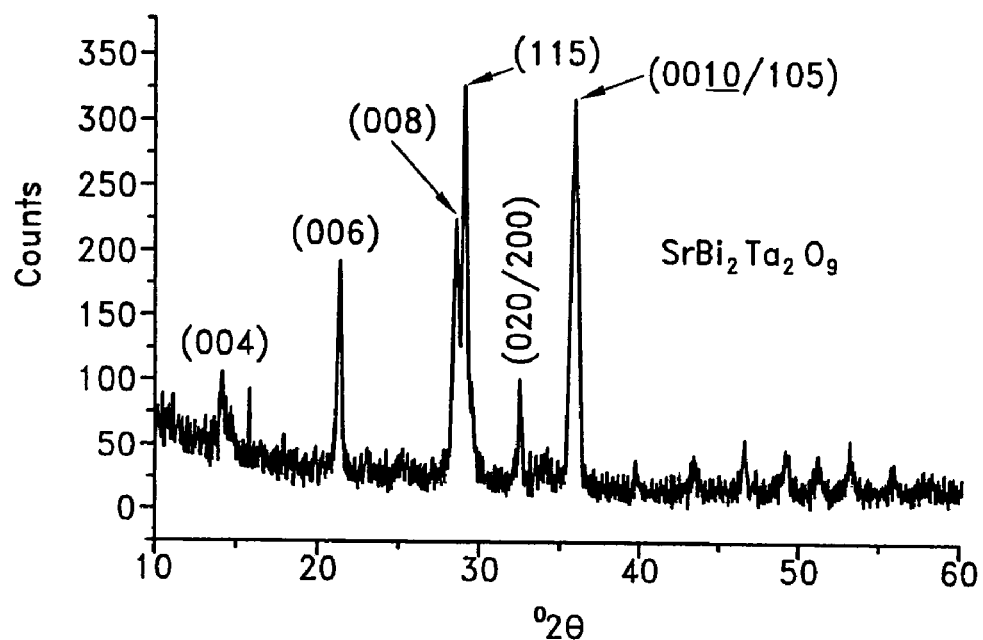
FIG. 3 shows an XRD diagram of an ALD SrBi$_2$Ta$_2$O$_9$ film annealed in air at 750° C.

A second approach was also used for depositing $SrBi_2Ta_2O_9$. Thus, amorphous laminate layers of Sr—Ta—O and Bi—O were grown. In this case, the overall composition was adjusted by varying the thicknesses of these layers, and the desired compound was formed by reacting the layers with each other in the following annealing steps. All the as-deposited SBT films were amorphous, but after annealing in air at 750° C. the desired ferroelectric phase was observed (FIG. 3).

EXAMPLE 4

Figure 4:
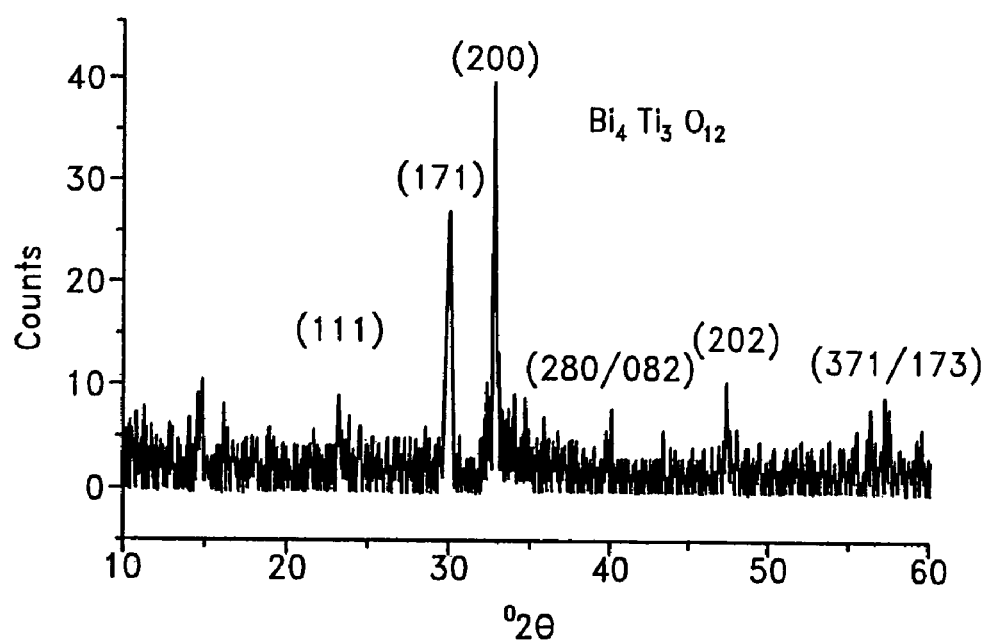
FIG. 4 shows an XRD diagram of an ALD Bi—Ti—O film annealed in air at 750° C.

Using the cycle mixing approach of Example 2 with $[Bi(btsa)_3\text{-}H_2O]$ and $[Ti(OMe)_4\text{-}H_2O]$ cycles, Bi—Ti—O films were grown at 200° C. $Bi_4Ti_3O_{12}$, a ferroelectric phase, was observed after annealing as-deposited films in air at 750° C. (FIG. 4).

Although this invention has been disclosed in the context of certain preferred embodiments and examples, it will be understood by those skilled in the art that the present invention extends beyond the specifically disclosed embodiments to other alternative embodiments and/or uses of the invention and obvious modifications thereof. Thus, it is intended that the scope of the present invention herein disclosed should not be limited by the particular disclosed embodiments described above, but should be determined only by a fair reading of the claims that follow.

What is claimed is:

1. A process for producing a bismuth-containing oxide thin film by Atomic Layer Deposition (ALD), wherein an organic bismuth compound having at least one silylamido ligand is used as a source material for the bismuth-containing oxide thin film, and wherein the bismuth-containing oxide thin film is deposited at a temperature of less than about 250° C.

2. The process according to claim 1, wherein the organic bismuth compound comprises a tris(bis(trialkylsilyl)amido) bismuth(III) compound, in which each alkyl is a lower alkyl group having 1 to 4 carbon atoms.

3. The process according to claim 2, wherein each alkyl is the same.

4. The process according to claim 2, wherein each alkyl is different.

5. The process according to claim 1, wherein the organic bismuth compound comprises a bismuth compound with 1 to 3 silylamido ligands having the formula of Equation 1:

—N(SiR$^1$R$^2$R$^3$)$_2$ (Equation 1)

wherein each R$^1$, R$^2$, R$^3$ is independently selected from the group consisting of:
 linear or branched C$_1$-C$_{20}$ alkyl and C$_1$-C$_{20}$ alkenyl groups,
 halogenated alkyl and halogenated alkenyl groups, wherein the halogenated alkyl and halogenated alkenyl groups have at least one hydrogen atom replaced with a fluorine, chlorine, bromine or iodine atom,
 carbocyclic groups; and
 heterocyclic groups.

6. The process according to claim 5, wherein at least one of R$^1$, R$^2$, and R$^3$ is a C$_1$-C$_{20}$ alkyl or a C$_1$-C$_{20}$ alkenyl selected from the group consisting of methyl, ethyl, n- and i-propyl, n-, sec- and t-butyl.

7. The process according to claim 5, wherein at least one of R$^1$, R$^2$, and R$^3$ is the carbocyclic group and the carbocyclic group is an aryl.

8. The process according to claim 5, wherein at least one of R$^1$, R$^2$, and R$^3$ is the carbocyclic group selected from the group consisting of phenyl, alkylaryl, and halogenated carbocyclic groups.

9. The process according to claim 1, wherein the bismuth oxide layer is deposited at a deposition temperature in the range of about 150° C. to about 220° C.

10. A process for depositing a bismuth oxide layer on a substrate by Atomic Layer Deposition (ALD) comprising:
 feeding into a reaction space a vapor phase pulse of an organic bismuth compound source material having at least one bis(trialkylsilyl)amido ligand; and
 pulsing into the reaction space a pulse of an oxygen source material capable of forming an oxide with the organic bismuth compound source material;
 wherein the bismuth oxide layer is deposited at a temperature of less than about 250° C.

11. The process according to claim 10, wherein the feeding and pulsing produce a ternary oxide thin film.

12. The process according to claim 11, wherein the ternary oxide thin film comprises a second metal source material selected from the group consisting of copper, titanium, tantalum, calcium, strontium, silicon and aluminum oxides.

13. The process according to claim 12, wherein the ternary oxide thin film comprises Bi$_4$Ti$_3$O$_{12}$.

14. The process according to claim 12, wherein the second metal oxide is deposited from a second metal source material selected from the group consisting of halides and metal organic compounds.

15. The process according to claim 14, wherein the second metal source material is selected from the group consisting of alkoxy, alkylamino, cyclopentadienyl, dithiocarbamate and betadiketonate compounds.

16. The process according to claim 14, wherein the second metal source material comprises a double metal precursor in which each molecule contains two metals in a discrete ratio.

17. The process according to claim 10, wherein the oxygen source material comprises one or more reactants selected from the group consisting of water, oxygen, hydrogen peroxide, aqueous solution of hydrogen peroxide, ozone, oxides of nitrogen, halide-oxygen compounds, peracids, alcohols, alkoxides, and oxygen-containing radicals.

18. The process according to claim 10, further comprising purging the reaction space with an inactive gas between pulses.

19. The process according to claim 10, wherein feeding into the reaction space the vapor phase pulse of the organic bismuth compound comprises mixing a carrier gas with the vapor phase pulse.

20. The process according to claim 10, wherein the bismuth oxide layer is deposited to serve as a functional layer which is selected from the group consisting of a ferroelectric layer, a dielectric layer, and a super-conducting layer.

21. The process according to claim 10, wherein the feeding and pulsing produce a multicomponent oxide thin film.

22. The process according to claim 21, wherein the multicomponent oxide thin film comprises at least two further metal oxides selected from the group consisting of copper, titanium, tantalum, calcium and strontium oxides.

23. The process according to claim 22, wherein the multicomponent oxide thin film is selected from the group consisting of Bi$_4$Ti$_3$O$_{12}$, (Bi,La)$_4$Ti$_3$O$_{12}$, SrBi$_2$Ta$_2$O$_9$, and Bi$_2$Sr$_2$CaCu$_2$O$_{8+x}$.

24. The process according to claim 23, wherein one or more tris(bis(trialkylsilyl)amido) bismuth(III) compound is selected from the group consisting of tris(bis(trimethylsilyl) amido) bismuth(III), tris(bis(ethyldimethylsilyl)amido) bismuth(III), tris(bis(n-butyldimethylsilyl)amido) bismuth(III), and tris(bis(triethylsilyl)amido) bismuth(III) and tris(bis(tri-n-propylsilyl)amido) bismuth(III).

25. A process for forming a bismuth-containing multicomponent oxide thin film by Atomic Layer Deposition (ALD) on a substrate in a reaction space, comprising:
 alternately feeding into the reaction space vapor phase pulses of a first metal source material, a second metal source material, and an oxygen source material capable of forming an oxide with the first metal source material and the second metal source material, wherein
 said first metal source material is an organic bismuth compound having at least one bis(trialkylsilyl)amido ligand, and
 said second metal source material is a volatile compound of a transition metal or a volatile compound of a main group metal;
 wherein the bismuth-containing multicomponent oxide thin film is deposited at a temperature of less than about 250° C.

26. The process according to claim 25, wherein one or more said second metal source material comprises one or more reactants selected from the group consisting of groups 1, 2, 3, 4, 5, 6, 7, 8, 9, 10, 11, 12, 13, and 14 of a periodic table of elements.

27. The process according to claim 25, wherein each vapor phase pulse of the first and second metal source materials is followed by a pulse of the oxygen source material.

28. The process according to claim 27, wherein a ratio of bismuth precursor cycles to second metal source cycles is from about 10:1 to about 1:10, wherein each cycle includes a pulse of an oxygen source material.

29. The process according to claim 28, wherein the ratio is from about 6:1 to about 1.5:1 and the multicomponent oxide thin film contains a stoichiometric surplus of 1 to 20 atomic percentage of bismuth.

30. The process according to claim 25, further comprising:
   depositing a first laminar metal oxide layer formed from the first metal source material and a second laminar metal oxide layer formed the second metal source material; and
   annealing a selected ratio of the first and second laminar layers to provide a ferroelectric phase.

31. The process according to claim 25, wherein the multicomponent oxide thin film is a ternary oxide film, the method further comprising:
   feeding alternating pulses of the organic bismuth compound and the second metal source material, followed by a pulse of the oxygen source material, into the reaction space to form an amorphous film; and
   annealing the amorphous film in the presence of an oxygen-containing gas.

32. The process according to claim 25, wherein the multicomponent thin film formed is selected from the group consisting of $Bi_4Ti_3O_{12}$, $(Bi,La)_4Ti_3O_{12}$, $SrBi_2Ta_2O_9$ and $Bi_2Sr_2CaCu_2O_{8+x}$.

* * * * *

UNITED STATES PATENT AND TRADEMARK OFFICE
CERTIFICATE OF CORRECTION

PATENT NO.         : 7,618,681 B2
APPLICATION NO. : 10/696591
DATED                  : November 17, 2009
INVENTOR(S)        : Marko Vehkamäki et al.

It is certified that error appears in the above-identified patent and that said Letters Patent is hereby corrected as shown below:

On Page 1, Item 73, Line 1, please change "N.V." to --N.V.,--

In Column 1, Line 55, please change "article[M." to --article [M.--

In Column 7, Line 2, please change "Eamshaw," to --Earnshaw,--

In Column 7, Line 25, please change "valuable," to --valuable--

In Column 10, Line 37, Claim 23, please change "SrBi $_2$" to --SrBi$_2$--

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,618,681 B2 Page 1 of 1
APPLICATION NO. : 10/696591
DATED : November 17, 2009
INVENTOR(S) : Vehkamäki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 560 days.

Signed and Sealed this

Twenty-sixth Day of October, 2010

David J. Kappos
*Director of the United States Patent and Trademark Office*